United States Patent [19]

Simmrock et al.

[11] 4,119,507

[45] Oct. 10, 1978

[54] PROCESS OF PRODUCING OLEFIN OXIDE

[75] Inventors: Karl Hans Simmrock, Dortmund; Gerhard Hellemanns, Marl, both of Germany

[73] Assignee: Metallgesellschaft Aktiengesellschaft, Frankfurt am Main, Germany

[21] Appl. No.: 852,753

[22] Filed: Nov. 18, 1977

[30] Foreign Application Priority Data

Dec. 22, 1976 [DE] Fed. Rep. of Germany ....... 2658189

[51] Int. Cl.² ............................................... C25B 3/02
[52] U.S. Cl. ...................................... 204/80; 204/98; 204/128
[58] Field of Search ........................... 204/98, 128, 80

[56] References Cited

U.S. PATENT DOCUMENTS

| 3,451,905 | 6/1969 | Kronig et al. | 204/80 |
| 3,455,797 | 7/1969 | Courtier | 204/80 |
| 3,497,431 | 2/1970 | Kronig et al. | 204/80 |
| 3,501,388 | 3/1970 | Kronig et al. | 204/79 |

Primary Examiner—R. L. Andrews
Attorney, Agent, or Firm—Burgess, Dinklage & Sprung

[57] ABSTRACT

The invention relates to a process for the manufacture of oxiranes of the formula

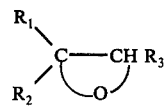

wherein $R_1$, $R_2$ and $R_3$ are hydrogen, methyl and/or ethyl and the total amount of carbon atoms of $R_1$, $R_2$ and $R_3$ is utmost 2 wherein olefin is subjected to an electrochemical system and reacts with a chlorine-containing anolyte to form an olefin chlorohydrin, with the latter subsequently reacted to form the oxirane.

The oxiranes are known compounds and are extensively used in the chemical field, for example, in the manufacture of detergents, polyethers, etc.

6 Claims, 1 Drawing Figure

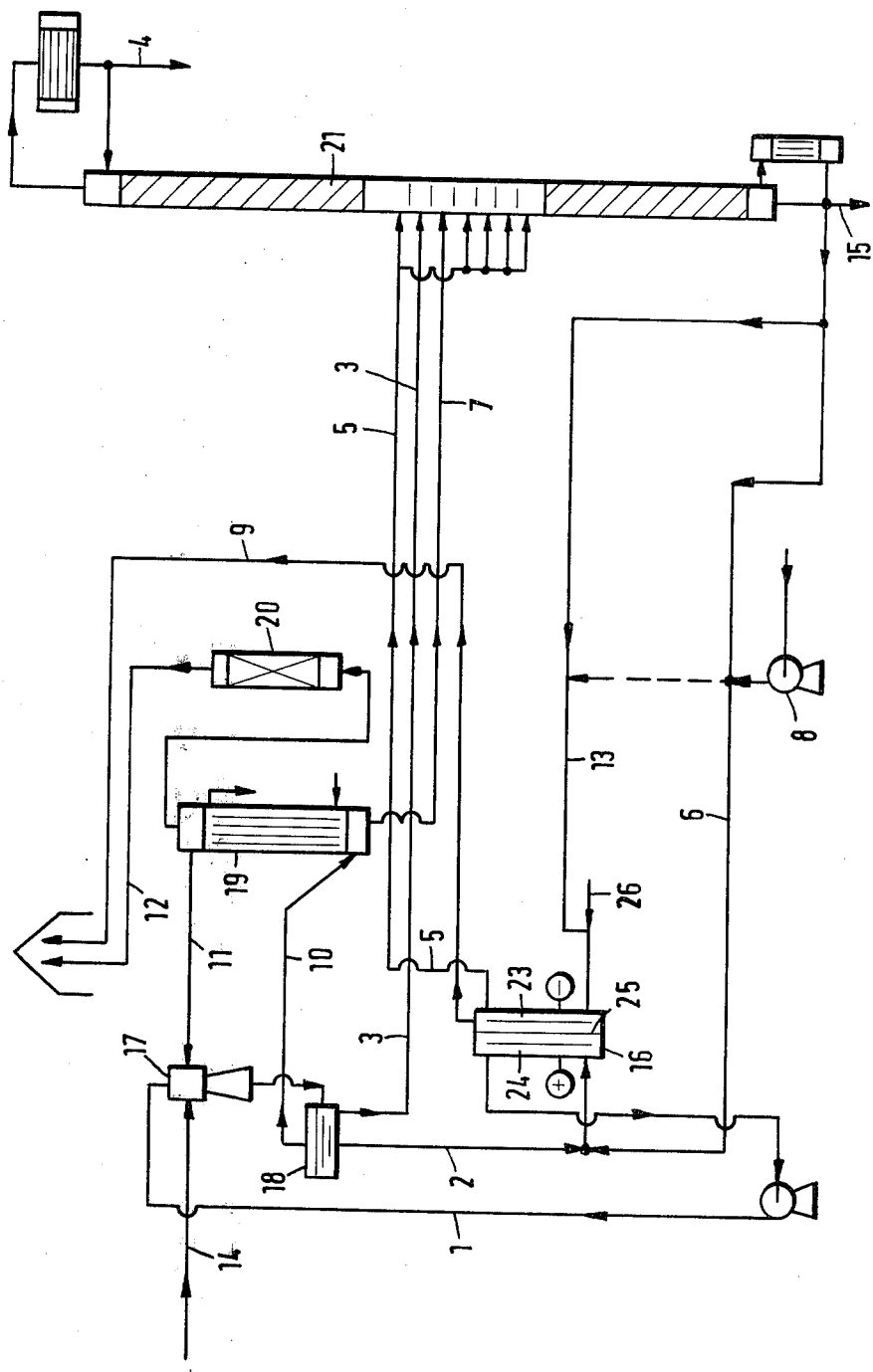

PROCESS OF PRODUCING OLEFIN OXIDE

This invention relates to an electrochemical process of producing oxiranes of the formula

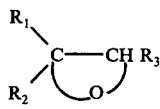

wherein $R_1$, $R_2$ and $R_3$ are substituents selected from the group consisting of hydrogen, methyl or ethyl and wherein the total amount of carbon atoms of $R_1$, $R_2$ and $R_3$ is utmost 2, from olefins by means of an electrochemical system which consists of an anode, a cathode and an intervening partition and which is supplied with an alkali metal chloride-containing (particularly sodium chloride- or potassium chloride-containing), aqueous electrolyte, wherein chlorine-containing anolyte and olefine are reacted to form olefin chlorohydrins in a reaction chamber disposed outside the electrochemical system, a partial stream of the chlorohydrin-containing solution which leaves the reaction chamber is returned to the anode chamber of the electrochemical system, another partial stream and alkaline catholyte withdrawn from the electrochemical system are reacted to form oxirane and alkali chloride, the oxirane is removed from the solution and the latter is then returned to the anode and cathode chambers of the electrochemical system.

It is known to produce olefin oxides (oxiranes), such as ethylene oxide or propylene oxide, from olefins by means of an electrochemical system which comprises an anode, a cathode and a diaphragm and is supplied with an electrolyte consisting of alkali chloride. In that known process the chlorine formed in the anode chamber is reacted with the olefin to form olefin chlorohydrin, which permeates the diaphragm and is dehydrochlorinated to form olefin oxide in the cathode chamber by a reaction with the alkaline solution formed therein. Hydrogen and olefin oxide are jointly withdrawn from the cathode chamber and are subsequently separated (Printed German application No. 12 52 649, Printed German application No. 12 43 170).

In another known process the transfer of olefin chlorohydrin from the anode chamber to the cathode chamber and the reaction in the cathode chamber to form olefin oxide are replaced by a reaction of the olefin in a reaction chamber disposed outside the electrochemical system. A circulation is maintained between said reaction chamber and the anode chamber of the electrochemical system, and part of the circulating stream is combined with the alkaline catholyte whereby the halohydrin contained in the anolyte is dehydrohalogenated to form olefin oxide (Printed German application No. 12 95 535).

Whereas the process described first requires a separation of hydrogen and olefin oxide in a separate step and involves a substantially uncontrolled dehydrohalogenation in the strongly alkaline catholyte, the process mentioned last affords the advantage that the reaction of olefin halohydrin and alkaline solution is mainly effected in special reaction chambers. On the other hand, it is not possible even in the latter process to prevent certain quantities of anolyte from entering the cathode chamber through the diaphragm so that minor quantities of olefin oxide are formed in the cathode chamber. For this reason a separation of hydrogen and olefin oxide is required also in that process. Besides, that quantity of olefin halohydrin which enters the cathode chamber through the diaphragm is not subjected to a controlled reaction so that glycols are formed in large quantities.

It is an object of the invention to provide a process which eliminates the disadvantages of the known processes, particularly the disadvantages stated hereinbefore, and which permits a controlled reaction of the olefin chlorohydrin which has been formed first.

In a process of the kind described first hereinbefore, this object is accomplished in accordance with the invention in that the electrolysis is carried out in an electrochemical system in which the anolyte and catholyte are separated by a membrane consisting of a cation-permeable polyfluorohydrocarbon which comprises electronegative groups.

The process according to the invention may be particularly used to produce oxirane, 2-methyl-oxirane, 2,2-dimethyl-oxirane, 2,3-dimethyl-oxirane, 2-ethyl-oxirane and the like.

Suitable polyfluorohydrocarbons are those which contain electronegative groups consisting, e.g. of sulfonic acid groups ($SO_3H$), carboxylic acid groups (COOH) and phosphonic acid groups ($PO_3H_2$) and consist of a compound having the general formula

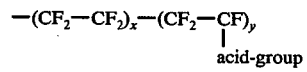

an equivalent weight of 700 to 1600, preferably 1000 to 1300, and a molecular weight of 50 000 to 1 500 000. The preferred polyfluorohydrocarbons contain sulfonic acid groups as electronegative groups (a product from Du Pont, marked "Nafion").

The membrane may consist of a material in which individual fluorine atoms of the polyfluorohydrocarbon chain have been replaced by other halogen atoms, preferably chlorine atoms.

The membrane is preferably supported by internal fixtures on the cathode side and/or anode side.

The electrodes may consist of the materials which are usual for that purpose. It is particularly suitable to use an anode consisting of titanium which is coated with ruthenium oxide and a cathode consisting of stainless steel.

The pH-value of the electrolyte solution fed to the anode chamber may be varied within wide limits and should be adjusted in any case so that a pH-value below 7, preferably in the range of 0,5 to 6, is obtained in the anode chamber, taking into account that the formation of chlorohydrin is accompanied by a release of hydrogen chloride. To stabilize the olefin chlorohydrin which is formed in the anode chamber and in the reaction chamber disposed outside the electrochemical system, that electrolyte solution is preferably adjusted to a pH-value below 3, e.g. by an addition of hydrogen chloride.

The electrochemical system will operate under favorable conditions if the electrolyte is at a temperature of 30° to 100° C., preferably 40° to 70° C., and has an alkali chloride concentration of 5 to 25% by weight, preferably 5 to 18% by weight. The operation in the lower range results in a high yield of olefin oxide and the operation in the upper range involves a formation of dichlorohydrocarbon to a certain extent. The electrochemical system may be operated under atmospheric or superatmospheric pressure.

The olefin to be reacted in the process according to the invention basically may be supplied to the anode chamber and/or to the reaction chamber disposed outside the electrochemical system. However, the olefin is preferably added in the reaction chamber, which suitably consists of a jet mixer, because this results in a low cell voltage for a given current density so that the current consumption is reduced.

To suppress the undesired formation of diol in the reaction chamber as far as possible, the alkaline catholyte to be reacted with the olefin chlorohydrin is preferably fed to this chamber in a plurality of partial streams and the olefin oxide which has been formed is continuously removed.

The invention will be explained more fully and by way of example with reference to the flow scheme and the examples.

Chlorine is formed in an electrochemical system 16, in which a membrane 25 divides a cathode chamber 23 and an anode chamber 24. This chlorine is fed in an aqueous solution and, if desired, in gaseous form as stream 1 to the reaction chamber, which consists of a jet mixer 17 and in which the chlorine reacts with olefin, which is fed with a surplus in conduit 14. The surplus olefin separates in the succeeding separator 18 from the aqueous solution and flows as stream 10 into the condenser 19, in which part of the condensible constituents, consisting mainly of dichloroolefins, chlorinated ethers, and olefin chlorohydrins, are separated. These products are fed as stream 7 to the rectifying column 21. Olefin which has been depleted from useful products flows back from the condenser 19 through olefin return conduit 11 to the jet mixer 17 and in the latter is reacted with fresh aqueous chlorine solution and any gaseous chlorine which is available. Two partial streams 2 and 3, which contain chlorohydrin, are withdrawn from the olefin separator 18. The larger partial stream 2 is fed to the electrochemical system 16 and is re-saturated therein with chlorine and the smaller partial stream 3 is fed to the rectifying column 21 for dehydrochlorination. The dehydrochlorination is effected in an alkaline medium by an addition of pure aqueous sodium hydroxide solution, which contains sodium chloride and which is withdrawn from the cathode chamber 23 of the electrochemical system 16 as stream 5. To prevent an undesired formation of glycols, a plurality of partial streams of said sodium hydroxide solution are contacted with the chlorohydrin from streams 3 and 7. A product stream 4 consisting of olefin oxide, water and chlorinated hydrocarbon, mainly olefin dichloride, is withdrawn from the top of the rectifier 21. Three partial streams consisting of an alkali chloride solution having a small glycol content are withdrawn from the lower end of said rectifier. Two partial streams 6 and 13 are fed to the anode and cathode chambers 24 and 23 of the electrochemical system 16, where they replace the above-described streams 5 and 3 in quantity so that the cycles including the electrochemical system and the chlorohydrin-producing stage, on the one hand, and the dehydrochlorinating stage, on the other hand, are completed.

A smaller partial stream 15 is withdrawn from the lower end of the rectifier 21.

In order to prevent a depletion of chloride in the catholyte and anolyte, chloride in a quantity which is equivalent to the olefin dichloride formed as a by-product is added preferably as hydrogen chloride through proportioning means 8 to stream 6 and, if desired, to stream 13. The water which is consumed in the process is supplied to the catholyte through conduit 26 and may be recovered to a large extent by the processing of the product stream 4, in order to decrease the sewage rate. Sodium chloride is dissolved in the recovered water, which is then added to the recycle stream 13. The hydrogen formed on the cathode side of the electrochemical system 16 is free from organic constituents and can be discharged without further treatment as stream 9 for further use, e.g. for hydrogenation or combustion.

The inert gas stream withdrawn from the condenser 19 still contains hydrocarbons. To prevent a pollution of air, these hydrocarbons are suitably absorbed by activated carbon in an adsorber 20 so that a pure inert gas stream 21 is released into the atmosphere.

EXAMPLE 1

The apparatus which is diagrammatically shown on the drawing was used to carry out the process.

The electrochemical system 16 comprised an anode of titanium coated with ruthenium dioxide, a cathode of V$_4$A steel, and a membrane 25 of polyfluorohydrocarbon, which contained sulfonic acid groups. Each electrode had an effective area of 6.67 dm$^2$ and the anode chamber 24 and cathode chamber 23 had volumes of 4.3 and 3.0 liters, respectively. The cell voltage was about 3.65 volts and the current density about 900 A/m$^2$ (corresponding to a current of 60 A). The electrochemical system was operated under atmospheric pressure.

The electrolyte consisted of a sodium/chloride solution containing 70 g/l NaCl. The catholyte and anolyte had pH-values of 12 and 0,8, respectively. The electrolyte was at a temperature of 55° C.

Propylene at a rate of 47 g/h was added in the jet mixer 17 to the anolyte stream 1, which then passed through the separator 18 and condenser 19, whereafter streams 3 and 7 having a total rate of 3 l/h were fed to rectifying column 21 and were reacted therein with the catholyte, which was fed at a rate of 20 l/h as stream 5 and then divided into five partial streams of 4 l/h each. Anolyte solution was circulated at a rate of 200 l/h in stream 1 and partial stream 2.

Solution at a rate of 0.1 l/h was removed through conduit 15. The remaining solution was recycled as stream 6 and 13 to the anode chamber 24 and to the cathode chamber 23. Hydrochloric acid at a rate of 0.1 l/h, corresponding to 5.8 g hydrogen chloride, was added to the stream 6 before it entered the anode chamber 24.

The product stream 4 contained
58.4 g/h propylene oxide
8.9 g/h 1.2-dichloropropane
1.7 g/h propane diol
about 1 g/h other organic compounds.

Based on the propylene feed, the reaction products were obtained with the following yields:
Propylene oxide: 90%
1.2-dichloropropane: 7%
propane diol: 2%
other organic compounds: 0.8%
The current efficiency amounted to 99%.

Example 2

The arrangement and basic process described in Example 1 were also used to react propylene to form propylene oxide. The conditions were as follows:

Cell voltage: 3.35 volts
Current density: 750 A/m² (corresponding to a current of 50 A)
Sodium chloride concentration in the electrolyte: 100 g/l
pH-value of anolyte: 0.8
pH-value of catholyte: 12
Electrolyte temperature: 50° C.
Propylene feed rate: 39 g/h
Hydrogen chloride feed rate: 8.9 g/h The electrochemical system was operated under atmospheric pressure.

The product stream 4 contained
45.2 g/h propylene oxide
13.6 g/h 1.2-dichloropropane
1.4 g/h propanediol
about 1 g other organic compounds.

The reaction products were obtained in the following yields, based on the propylene feed:
Propylene oxide: 84%
1.2-dichloropropane: 13%
Propanediol: 2%
other organic compounds: 0.9%
The current efficiency was about 99%.

Example 3

The arrangement and basic process described in Example 1 were also used to react ethylene to form ethylene oxide. The conditions were as follows:

Cell voltage: 3.14 volts
Current density: 600 A/m² (corresponding to a current of 40 A)
Sodium chloride concentration in the Electrolyte: 130 g/l
pH-value of anolyte: 0.9
pH-value of catholyte: 11.5
Electrolyte temperature: 45° C.
Ethylene feed rate: 21 g/h
Hydrogen chloride feed rate: 12.1 g/h The electrochemical system was operated under atmospheric pressure.

The product stream 4 contained
24.8 g/h ethylene oxide
16.3 g/h 1.2-dichloroethane
0.9 g/h ethylene glycol
about 0.5 g/h other organic compounds.

The reaction products were obtained in the following yields, based on the ethylene feed:
Ethylene oxide: 75%
1.2-dichloroethane: 22%
Ethylene glycol: 2%
Other organic compounds: 1%
The current efficiency was about 99%.

What is claimed is:

1. An electrochemical process of producing oxiranes of the formula

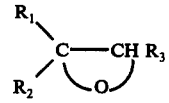

wherein $R_1$, $R_2$ and $R_3$ are substituents selected from the group consisting of hydrogen, methyl or ethyl and wherein the total amount of carbon atoms of $R_1$, $R_2$ and $R_3$ is utmost 2, from olefins by means of an electrochemical system which consists of an anode, a cathode and an intervening partition and which is supplied with an alkali metal chloride-containing, aqueous electrolyte, wherein chlorinecontaining anolyte and olefin are reacted to form olefin chlorohydrin in a reaction chamber disposed outside the electrochemical system, a partial stream of the chlorohydrin-containing solution which leaves the reaction chamber is returned to the anode chamber of the electrochemical system, another partial stream and alkaline catholyte withdrawn from the electrochemical system are reacted to form oxirane and alkali chloride, the oxirane is removed from the solution and the latter is then returned to the anode and cathode chambers of the electrochemical system, characterized in that the electrolysis is carried out in an electrochemical system in which the anolyte and catholyte are separated by a membrane consisting of a cationpermeable polyfluorohydrocarbon which contains electronegative groups.

2. A process according to claim 1, characterized in that the electrolysis is carried out in an electrochemical system in which the anolyte and catholyte are separated by a membrane of cation-permeable polyfluorohydrocarbon which contains sulfo groups.

3. A process according to claim 1, characterized in that the electrolyte solution contained in the anode chamber is adjusted to pH-value below 3.

4. A process according to claim 1, characterized in that the alkaline catholyte is fed in a plurality of partial streams and the resulting oxirane is continuously removed.

5. A process according to claim 1, characterized in that the olefin is ethylene.

6. A process according to claim 1, characterized in that the olefin is propylene.

* * * * *